(12) United States Patent
Shimada et al.

(10) Patent No.: US 6,491,675 B1
(45) Date of Patent: Dec. 10, 2002

(54) DISPOSABLE PULL-ON DIAPER HAVING DISPOSAL SECURING MEANS

(75) Inventors: Takaaki Shimada, Kagawa-ken (JP); Toshio Inoue, Kagawa-ken (JP); Seiji Suzuki, Kagawa-ken (JP); Kenji Nakamura, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 09/686,933

(22) Filed: Oct. 12, 2000

(30) Foreign Application Priority Data

Oct. 14, 1999 (JP) .............................. 11-291993

(51) Int. Cl.⁷ .......................... A61F 13/15; A61F 13/20
(52) U.S. Cl. ............................ 604/385.13; 604/385.01; 604/396
(58) Field of Search .................. 604/385.01–385.06, 604/385.13–385.14, 385.201, 385.22, 385.24–387, 389–396, FOR 103, FOR 104

(56) References Cited

U.S. PATENT DOCUMENTS 3,920,018 A  *  11/1975  Schaar ...................... 604/396

FOREIGN PATENT DOCUMENTS

| DE | 196 54 456 | 7/1998 |
| EP | 0 732 094 | 9/1996 |
| EP | 0 875 226 | 11/1998 |
| EP | 0 965 317 | 12/1999 |
| JP | 7-39816 | 7/1995 |

OTHER PUBLICATIONS

Patent Abstracts of Japan, vol. 1999, No. 09, Jul. 30, 1999 & JP 11 099172, Apr. 13, 1999.
Patent Abstracts of Japan, vol. 1996, No. 12, Dec. 26, 1996 & JP 08 215247, Aug. 27, 1996.

* cited by examiner

*Primary Examiner*—Glenn K. Dawson
*Assistant Examiner*—K. M. Reichle
(74) *Attorney, Agent, or Firm*—Lowe Hauptman Gilman & Berner, LLP

(57) ABSTRACT

A disposable pull-on diaper includes a liquid-pervious topsheet, a liquid-impervious backsheet and a liquid-absorbent core disposed therebetween. The diaper has a waist-hole and a pair of leg-holes. The diaper is provided on one of a front half or a rear half thereof with at least one elastically stretchable fastening member transversely extending across a longitudinal center line of the diaper, and a hook member which lies on the longitudinal center line to catch the fastening member. The fastening member has transversely opposite end portions secured to the diaper, and a transversely intermediate portion exposed on an outer surface of the backsheet. After use, the used diaper is rolled-up with an outer peripheral surface thereof surrounded by the intermediate portion, and the intermediate portion is caught by the hook to secure the used diaper in the rolled-up state.

8 Claims, 8 Drawing Sheets

DISPOSABLE PULL-ON DIAPER HAVING DISPOSAL SECURING MEANS

BACKGROUND OF THE INVENTION

This invention relates to a disposable pull-on diaper adapted to absorb and contain body fluids discharged thereon, and more particularly, to such a diaper having disposal securing means.

Japanese Utility Model Application Disclosure No. 1995-39816 describes a disposable pull-on diaper comprising a liquid-pervious topsheet, a liquid-impervious backsheet and a liquid-absorbent core disposed between the sheets to define, in a longitudinal direction of the diaper, a front waist region, a rear waist region and a crotch region extending between the waist regions. A pair of end flaps lying in the front and rear waist regions, respectively, define a waist-hole and a pair of side flaps define a pair of leg-holes.

The end flaps are provided therein with a plurality of elastically stretchable members one of which can be drawn out from the end flaps through a cut formed in one of the end flaps. The elastically stretchable member drawn out from the end flaps serves as a rubber band used to fasten the diaper which has been used and rolled up. Thus, the used diaper can be maintained in a rolled up and fastened state for disposal.

In the diaper disclosed above, the waist-hole of the used and rolled up diaper can be closed only in the vicinity of the longitudinal center line along which the elastic member lies when the used diaper is rolled up with the waist-hole facing outside. The elastic members have almost no fastening effect on transversely opposite sides of the waist-hole which are remote from the vicinity of the longitudinal center line. Consequently, the rolled up diaper tends to be unrolled and the waist-hole tends to be opened. As a result, excretion may leak together with its odor outside.

SUMMARY OF THE INVENTION

It is an object of this invention to provide a disposable pull-on diaper which can be rolled up for disposal after use without any apprehension that excretion and odor might leak outside.

This and other objects of the present invention are achieved by a disposable pull-on diaper which comprises a diaper body, at least one elastically stretchable fastening member, and a hook member. The diaper body has, in a longitudinal direction thereof, a front waist region, a rear waist region and a crotch region extending therebetween. The diaper body comprises a liquid-pervious topsheet, a liquid-impervious backsheet and a liquid-absorbent core disposed between the topsheet and backsheet. The front and rear waist regions are joined together along respective transversely opposite side edges thereof to define a waist-hole and a pair of leg-holes. At least one elastically stretchable fastening member is provided on one of a front half of the diaper body which front half extends from a transverse center line of the diaper bisecting the crotch region toward the front waist region, and a rear half of the diaper body which rear half extends from the transverse center line toward the rear waist region. The at least one elastically stretchable fastening member extends transversely of the diaper body across a longitudinal center line bisecting a dimension between the transversely opposite side edges of the front and rear waist regions. The at least one elastically stretchable fastening member comprises opposite end portions and an intermediate portion extending between the opposite end portions. The opposite end portions are directly secured to the diaper body whereas the intermediate portion is not directly secured to and separable from the diaper body. The intermediate portion of the fastening member is exposed on an outer surface of the backsheet. A hook member is provided on the longitudinal center line in the one of the front and rear halves to catch the intermediate portion of the fastening member when the diaper body is rolled up, after use, with the intermediate portion of the fastening member extending around the rolled diaper body.

In accordance with an aspect of the present invention, the at least one elastically stretchable fastening member includes at least a pair of elastically stretchable fastening members extending in parallel and spaced from each other in the longitudinal direction. Preferably, the intermediate portions of the pair of elastically stretchable fastening members have different dimensions.

In accordance with another aspect of the present invention, the at least one elastically stretchable fastening member includes at least a pair of elastically stretchable fastening members, the intermediate portions of the pair of elastically stretchable fastening members intersect each other in a vicinity of the longitudinal center line.

In accordance with a further aspect of the present invention, the intermediate portion extends between transversely opposite side edges of the core.

In accordance with yet another aspect of the present invention, the at least one fastening member is secured under no tension to the diaper body.

The above mentioned object and other objects of the present invention are also achieved by a disposable pull-on diaper which comprises a diaper body and securing means for securing the diaper body in a rolled-up state, after use. The diaper body has, in a longitudinal direction thereof, a front waist region, a rear waist region and a crotch region extending therebetween, the front and rear waist regions being joined together along respective transversely opposite side edges thereof to define a waist-hole and a pair of leg-holes. The securing means includes an elastically stretchable fastening member and a hook member. The elastically stretchable fastening member is provided in an upper zone of one of the front and rear waist regions and extends transversely of the diaper body, opposite ends of the elastically stretchable fastening member are secured to the diaper body at locations adjacent the transversely opposite side edges of the front and rear waist regions. The hook member is provided in a middle zone of the one of the front and rear waist regions between the elastically stretchable fastening member and the crotch region, so as to hook the elastically stretchable fastening member which extends around the rolled-up diaper body, after use.

In accordance with a further aspect of the present invention the diaper body has an outer surface and an inner surface. The opposite ends of the elastically stretchable fastening member are laid between the outer and inner surfaces. The elastically stretchable fastening member further includes a middle portion extending between the opposite ends. The middle portion is exposed on the outer surface of the diaper body in the one of the front and rear waist regions.

In the disposable diaper of the present invention, regions of the diaper which are placed upon each other on the outer peripheral surface of the diaper and rolled up for disposal are collapsed, closed and reliably maintained in the rolled-up state by the fastening member. The fastening member in this state is branched in at least two sections by the hook member and is wound around the outer peripheral surface of the rolled up diaper. The diaper is thus held in the rolled-up state by the at least two sections of the fastening member, and is restrained from being unrolled in a more secure manner than the above mentioned prior art. In this way, it is very unlikely that the rolled diaper might be partially reopened, and excretion and odor might leak outside.

DETAILED DESCRIPTION OF THE PREFERRED EMBODIMENTS

Details of a disposable pull-on diaper according to this invention will be more fully understood from the description given hereunder with reference to the accompanying drawings.

Figure 1:
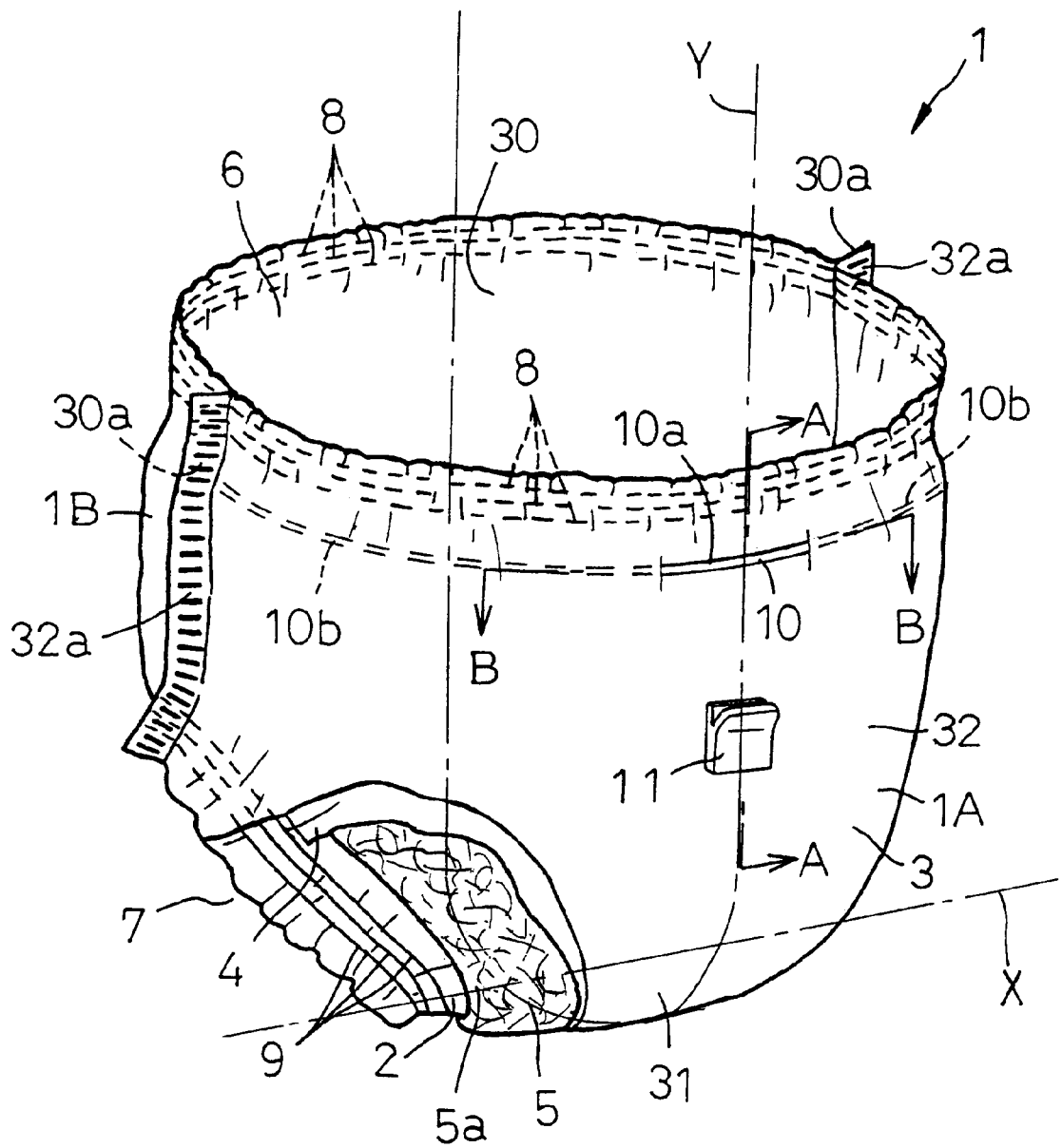
FIG. 1 is a partially cutaway perspective view showing one embodiment of a disposable pull-on diaper according to this invention.
Figure 2:
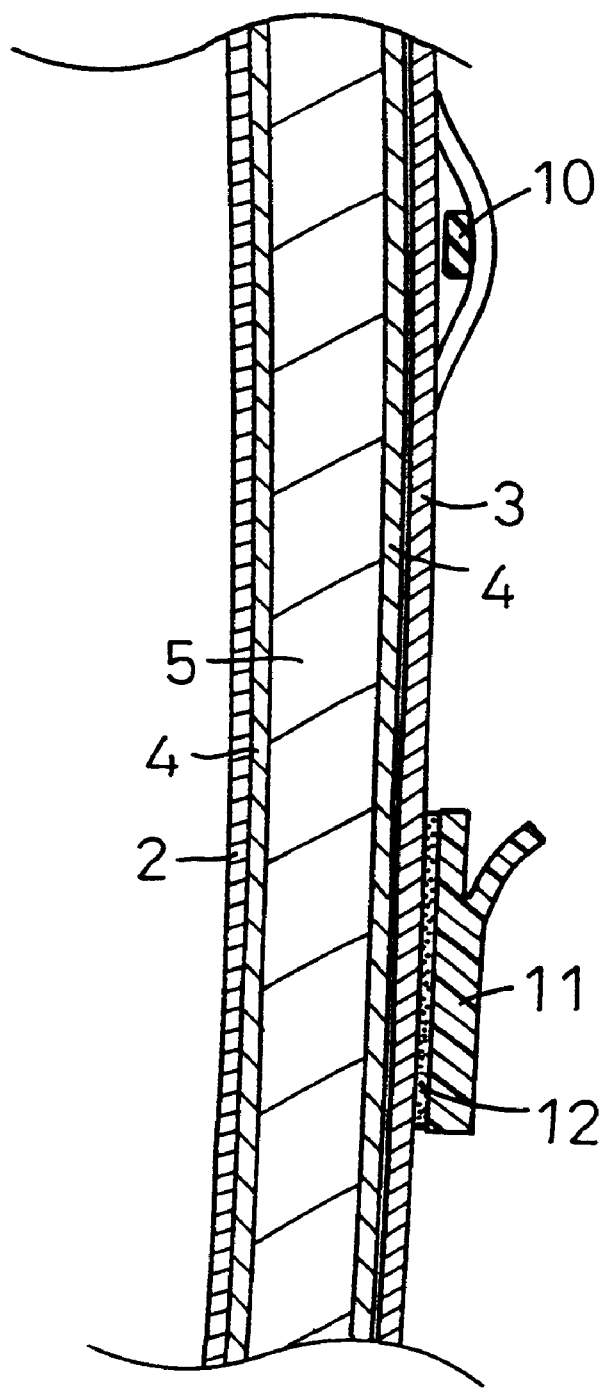
FIG. 2 is a sectional view taken along line A—A in FIG. 1.
Figure 3:
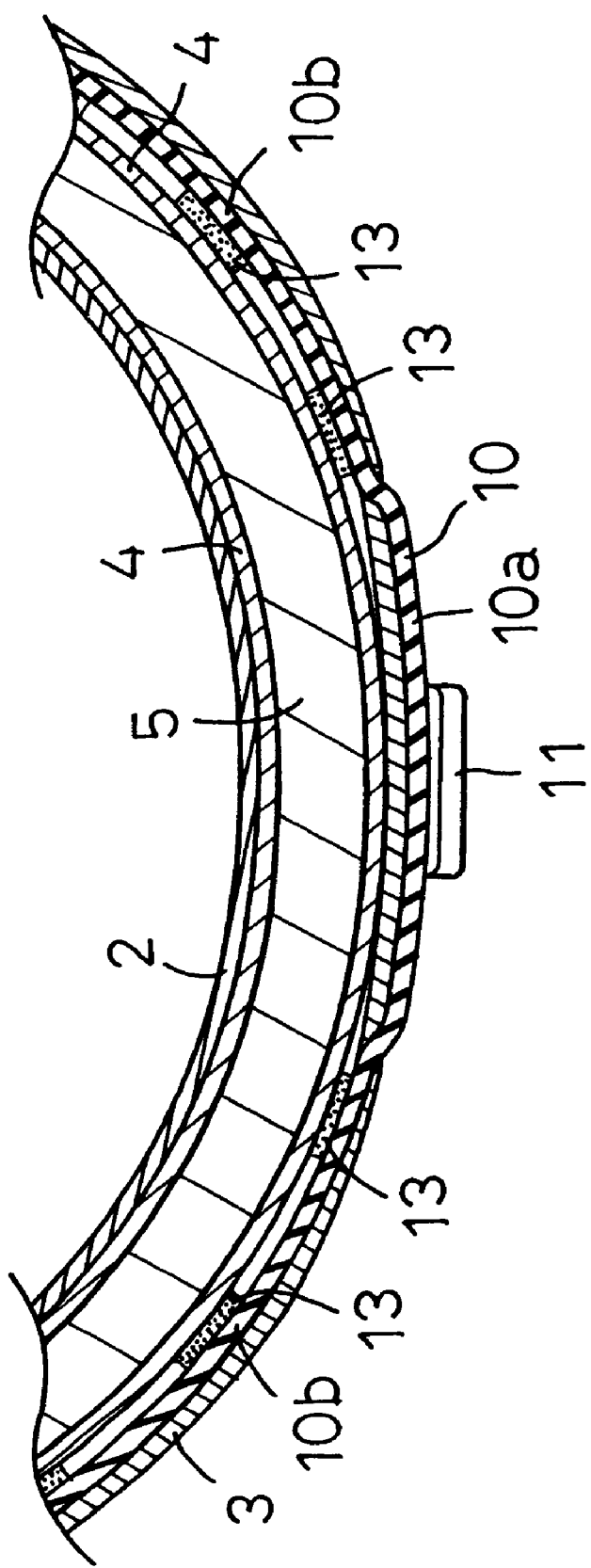
FIG. 3 is a sectional view taken along line B—B in FIG. 1.

FIG. 1 is a partially cutaway perspective view showing one embodiment of a disposable pull-on diaper according to this invention, FIG. 2 is a sectional view taken along line A—A in FIG. 1, and FIG. 3 is a sectional view taken along line B—B in FIG. 1. The diaper 1 comprises a liquid-pervious topsheet 2 (best seen in FIG. 2), a liquid-impervious backsheet 3 and a liquid-absorbent core 5 disposed between the top- and backsheets 2, 3 and entirely covered with and joined to a liquid-absorbent sheet 4. The absorbent sheet 4 is joined to the inner surface of at least one of the top- and backsheets 2, 3. The diaper 1 is composed of, in its longitudinal direction, a front waist region 30, a rear waist region 32 and a crotch region 31 extending between the front and rear waist regions 30, 32. The front and rear waist regions 30, 32 are put flat and joined together along their respective transversely opposite side edges 30a, 30a; 32a, 32a to define a waist-hole 6 and a pair of leg-holes 7, 7 (only one leg hole is shown in FIG. 1).

The waist-hole 6 is provided along its peripheral edge with a plurality of elastically stretchable members 8 which are disposed between the top- and backsheets 2, 3, and each of the leg-holes 7 is provided along its peripheral edge with a plurality of elastically stretchable members 9 which are disposed between the top- and backsheets 2, 3. The elastically stretchable members 8, 9 are secured under tension to the inner surface of at least one of the top- and backsheets 2, 3.

The rear waist region 32 is provided with a single elastically stretchable member 10 (fastening member) used to fasten the used diaper 1 in a rolled up state, and a hook member 11 (catching member) adapted to catch the elastic member 10 for fastening the used diaper in its rolled up state.

The elastic fastening member 10 transversely extends across a longitudinal center line Y—Y bisecting a dimension between transversely opposite side edges 32a, 32a of the rear waist region 32. The elastic member 10 comprises transversely opposite end portions 10b, 10b adjacent the respective side edges 32a, 32a, and a transversely intermediate portion 10a extending between the opposite end portions 10b, 10b and exposed on the outer surface of the backsheet 3. The transversely opposite end portions 10b, 10b of the elastic fastening member 10 are disposed between the backsheet 3 and the absorbent sheet 4 and secured, preferably under no tension, to the absorbent sheet 4 by means of adhesive 13 so that the portions 10b, 10b can not be readily peeled off the diaper 1. The transversely intermediate portion 10a of the elastic fastening member 10 extends between transversely opposite side edges 5a, 5a of the core 5.

The hook member 11 is secured to the outer surface of the backsheet 3 by means of adhesive 12 at a position defined between the elastic fastening member 10 and the crotch region 31 and is preferably closer to the crotch region 31 than to the member 10. A side of the hook member 11 facing the waist-hole 6 is bifurcated upwardly of the diaper 1.

Figure 4:
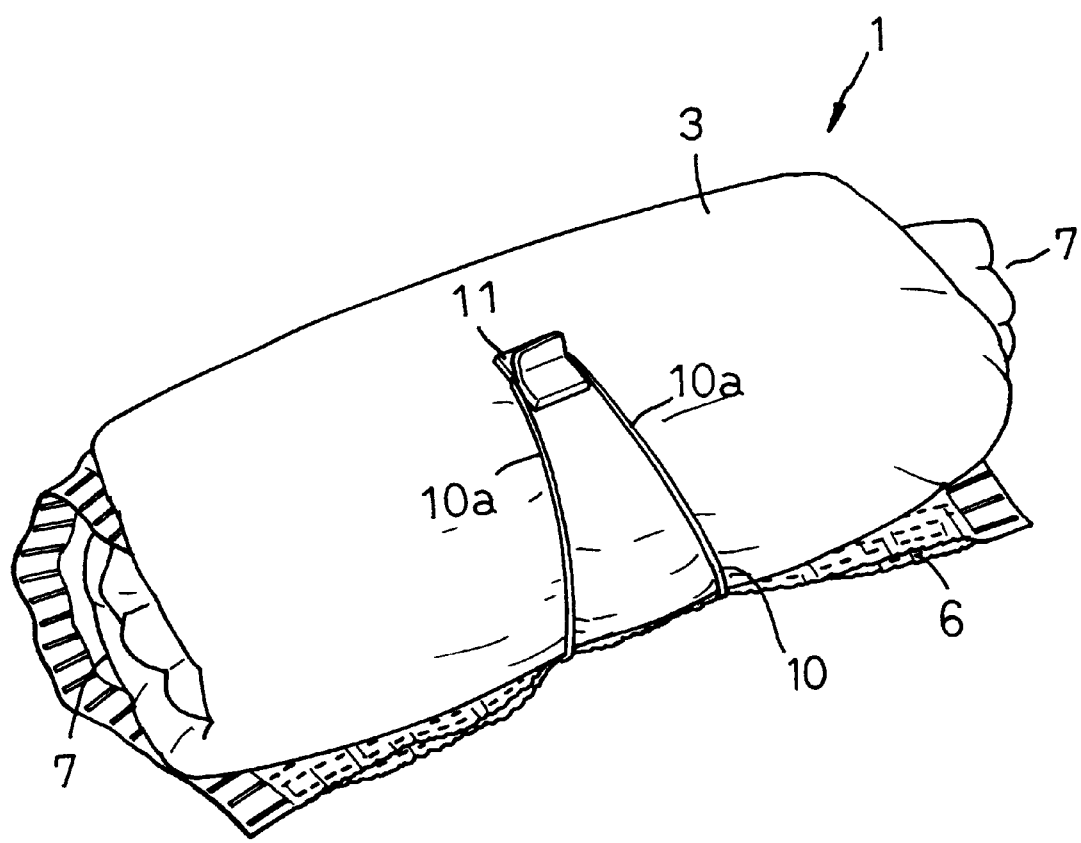
FIG. 4 is a perspective view showing the diaper of FIG. 1 in a rolled up state for disposal after use.

FIG. 4 is a perspective view showing the diaper of FIG. 1 in a rolled up state for disposal after use. As shown, the diaper 1 is rolled up from the crotch region 31 in the longitudinal direction with the waist-hole 6 facing outside. The stretched elastic fastening member 10 is laid around an outer peripheral surface of the rolled up diaper 1 and the transversely intermediate portion 10a is caught by the hook member 11.

The elastic fastening member 10 has an elastic stretchability sufficient to surround the outer peripheral surface of the rolled up diaper 1 with the transversely intermediate portion 10a. As will be apparent from FIG. 4, the diaper 1 is held in its rolled up state by the transversely intermediate portion 10a of the elastic member 10 branched in two sections from the hook member 11 with the waist-hole 6 of the diaper 1 reliably collapsed by the transversely intermediate portion 10a of the elastic member 10. In this way, the elastic fastening member 10 is capable of restraining the rolled up diaper 1 from being unrolled and thereby preventing the waist-hole from being opened in a more secure manner than the aforesaid prior art.

The transversely intermediate portion 10a of the elastic fastening member 10 extends between the transversely opposite side edges 5a, 5a of the core 5 and therefore it is not apprehended that the transversely intermediate portion 10a might be separated from the respective transversely opposite side edges 30a, 30a; 32a, 32a of the front and rear waist regions 30, 32 as the elastic fastening member 10 is pulled.

While the elastic fastening member 10 as well as the hook member 11 are illustrated provided on the rear waist region 32, the members 10, 11 may be provided on either the front half 1A or a rear half 1B with respect to a transverse center line X—X extending across the middle of the crotch region 31.

Figure 5:
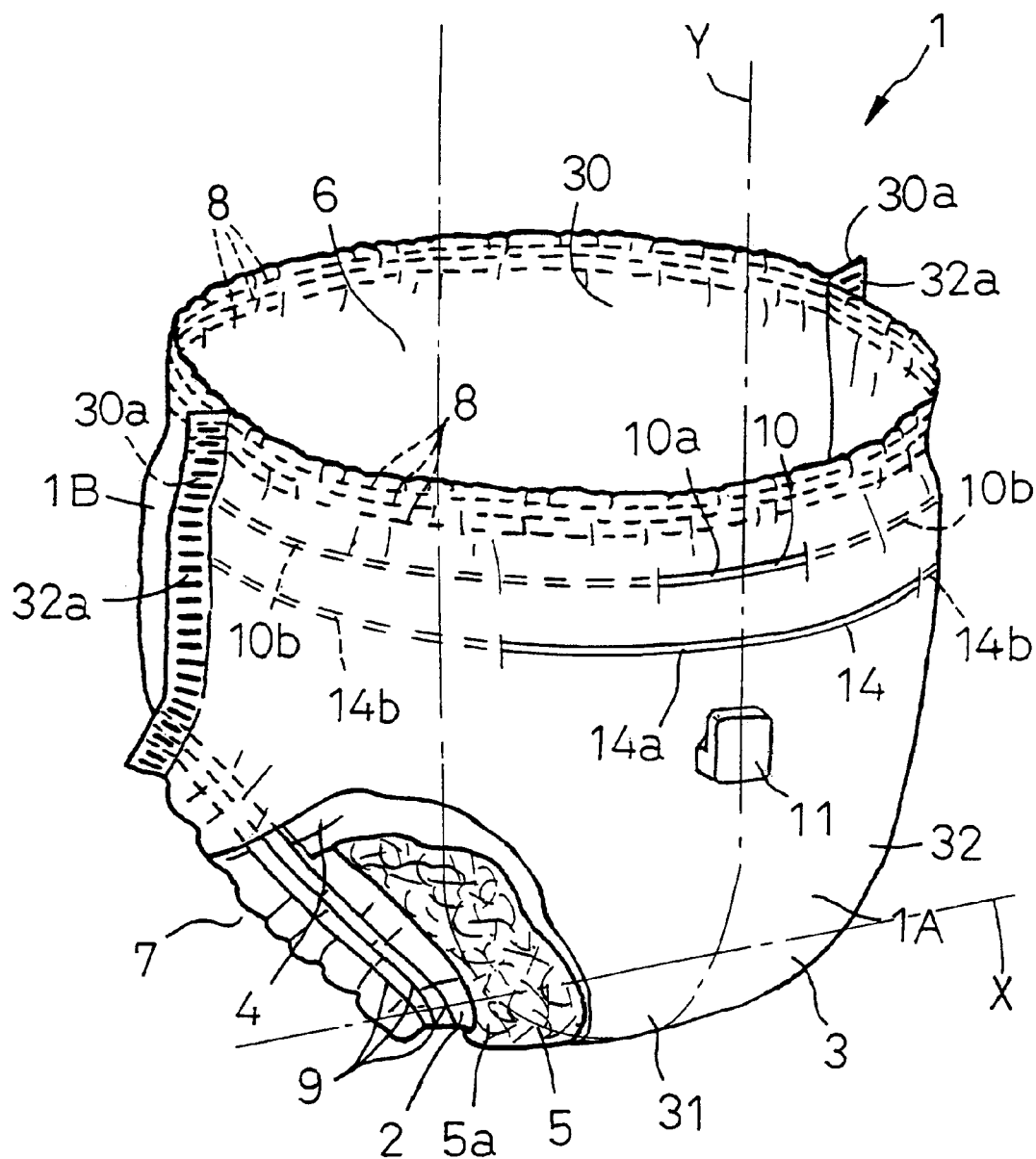
FIG. 5 is a view similar to FIG. 1 showing another embodiment of the diaper according to this invention.
Figure 6:
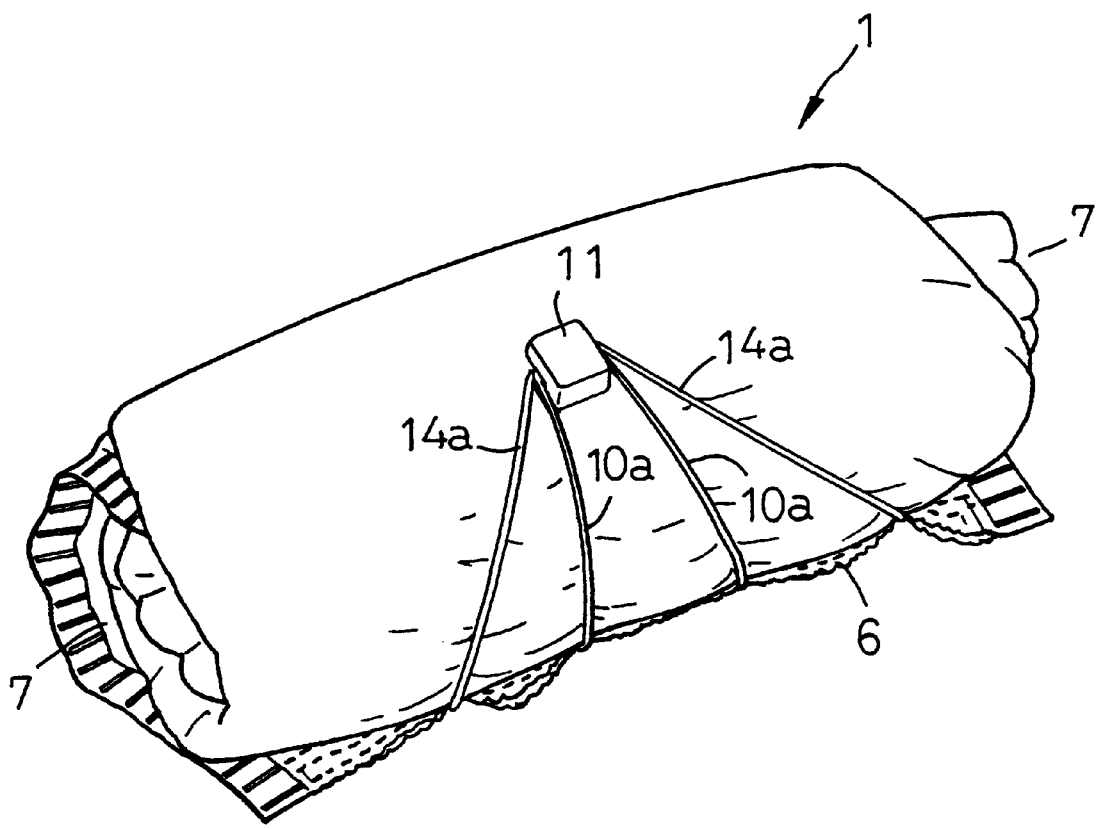
FIG. 6 is a perspective view showing the diaper of FIG. 5 in a rolled up state for disposal after use.

FIG. 5 is a view similar to FIG. 1 showing another embodiment of the diaper according to this invention and FIG. 6 is a perspective view showing the diaper of FIG. 5 in a rolled up state for disposal after use. This embodiment is similar to the one shown by FIG. 1 in that the diaper 1 comprises the liquid-pervious topsheet 2, the liquid-impervious backsheet 3 and the liquid-absorbent core 5 disposed between the top- and backsheets 2, 3 so as to define, in a longitudinal direction of the diaper, the front waist region 30, the rear waist region 32, the crotch region 31 extending between the front and rear waist regions 30, 32, the waist-hole 6 and the pair of leg-holes 7, 7.

The rear waist region 32 of the diaper 1 is provided with two elastic fastening members 10, 14 and a hook member 11. The hook member 11 is L-shaped in cross-section and formed with a gap between a part of the hook member 11 facing the waist-hole 6 and the backsheet 3. The hook is adapted to catch the elastic fastening members 10, 14.

The elastic fastening members 10, 14 transversely extend across the longitudinal center line Y—Y in parallel to each other with a predetermined spacing from each other. The elastic fastening members 10, 14 respectively comprise their transversely opposite side portions 10b, 10b; 14b, 14b lying adjacent the transversely opposite side edges 32a, 32a of the rear waist region 32 and their transversely intermediate portions 10a, 14a extending between the transversely opposite side portions 10b, 10b; 14b, 14b, respectively. Both portions 10a, 14a are exposed on the outer surface of the backsheet 3. The transversely opposite end portions 10b, 10b; 14b, 14b of the respective elastic fastening members 10, 14 are disposed between the backsheet 3 and the absorbent sheet 4 and secured to the absorbent sheet 4 by means of adhesive (not shown). The transversely intermediate portions 10a, 14a of the respective elastic fastening member 10, 14 extend between the transversely opposite side edges 5a, 5a of the core 5. The transversely intermediate portion 14a of the lower elastic fastening member 14 has a dimension longer than a dimension of the transversely intermediate portion 10a of the upper elastic fastening member 10.

Referring to FIG. 6, the diaper 1 is rolled up from the crotch region 31 toward the waist-hole 6 in the longitudinal direction with the waist-hole 6 facing outside. As will be apparent from FIG. 6, the stretched elastic members 10, 14 are wound around the outer peripheral surface of the rolled up diaper 1 as the transversely intermediate portions 10a, 14a of the respective elastic fastening members 10, 14 are caught by the hook member 11.

The waist-hole 6 of the diaper 1 is collapsed by the respective transversely intermediate portions 10a, 14a of the elastic fastening members 10, 14. Each of the intermediate portions 10a, 14a are branched in two sections by the hook member 11. Thus, the rolled up diaper 1 is fastened and maintained by four lines of elastic members 10a, 10a; 14a, 14a in the rolled up state, and still further restrained from being unrolled.

The respective elastic members 10, 14 are longitudinally spaced from each other and their transversely intermediate portions 10a, 14a are different in their dimension. Once the transversely intermediate portions 10a, 14a have been caught by the hook member 11, it is ensured that the respective two branches of the transversely intermediate portions 10a, 14a, i.e., four branches 10a, 10a; 14a, 14a extending from the hook member 11, are reliably spaced one from another and can effectively hold the diaper 1 in its rolled up state.

Figure 7:
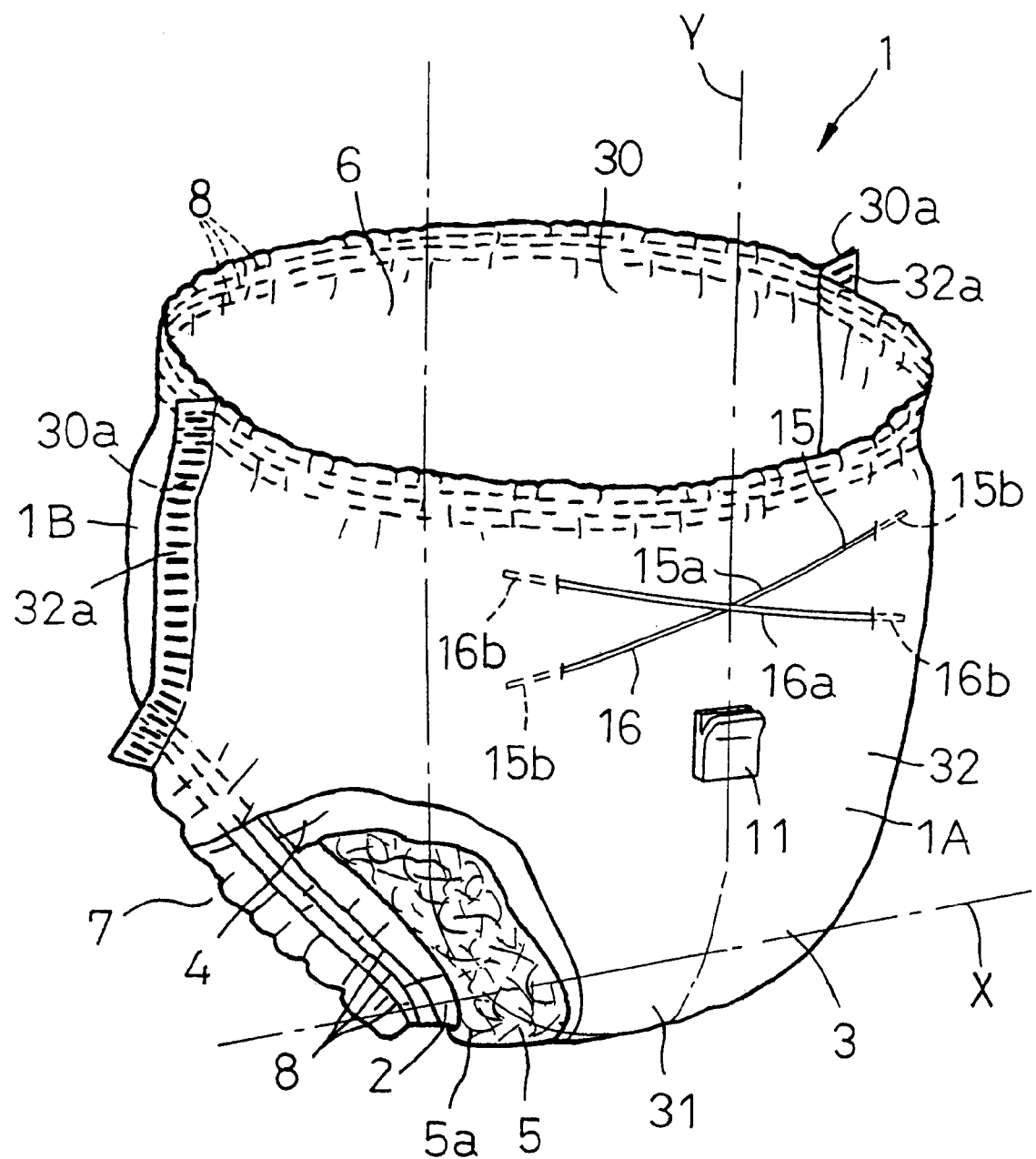
FIG. 7 is a view similar to FIGS. 1 and 5 showing still another embodiment of the diaper according to this invention.
Figure 8:
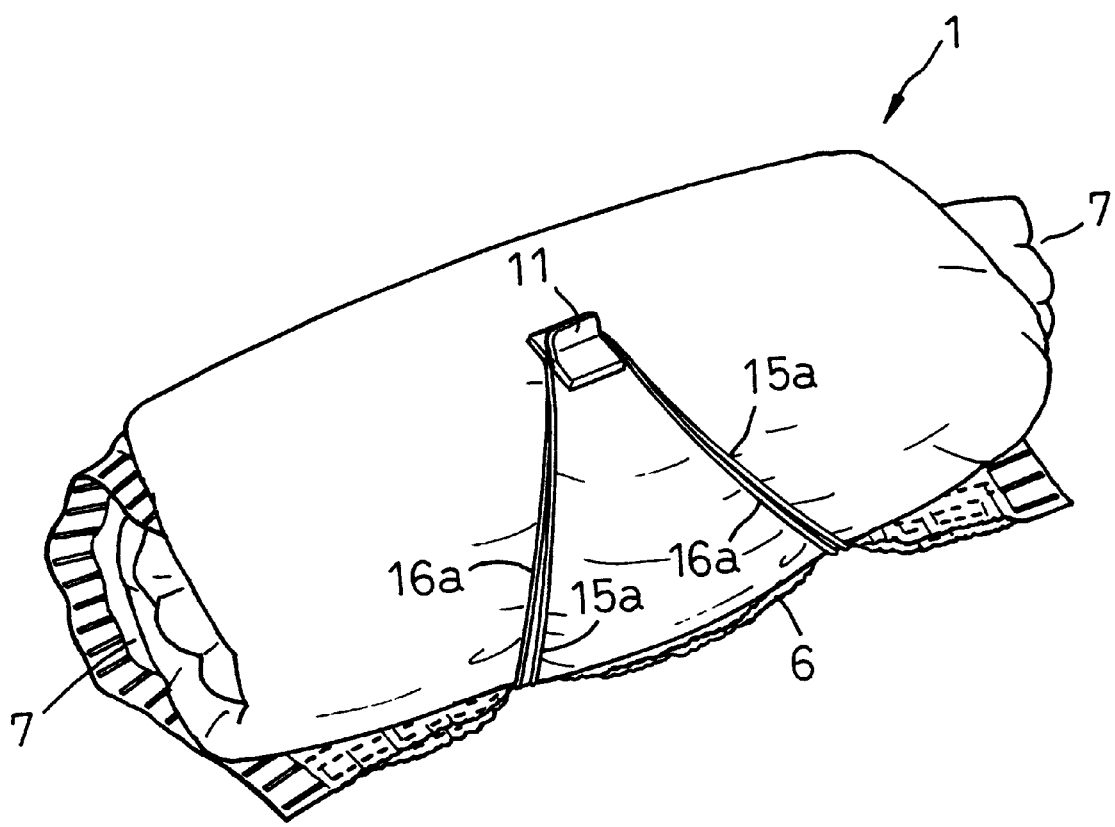
FIG. 8 is a perspective view showing the diaper of FIG. 7 in a rolled up state for disposal after use.

FIG. 7 is a view similar to FIGS. 1 and 5 showing still another embodiment of the diaper according to this invention, and FIG. 8 is a perspective view showing the diaper of FIG. 7 as rolled up for its disposal after use. The diaper 1 according to this embodiment is similar to those shown by FIGS. 1 and 5 in that the diaper 1 comprises the liquid-pervious topsheet 2, the liquid-impervious backsheet 3 and the liquid-absorbent core 5 disposed between the topsheets and backsheets 2, 3 so as to define, in its longitudinal direction, the front waist region 30, the rear waist region 32, the crotch region 31 extending between the front and rear waist regions 30, 32, the waist-hole 6 and the pair of leg-holes 7, 7.

The rear waist region 32 of the diaper 1 is provided with two elastic fastening members 15, 16 and the hook member 11. Aside of the hook member 11 facing the waist-hole 6 is bifurcated upwardly of the diaper 1.

The elastic fastening members 15, 16 transversely extend and obliquely intersect each other across the longitudinal center line Y—Y instead of extending in parallel to each other orthogonally across the longitudinal center line Y—Y. The elastic fastening members 15, 16 respectively comprise respective transversely opposite end portions 15b, 15b; 16b, 16b and respective transversely intermediate portions 15a, 16a extending between the transversely opposite end portions 15b, 15b; 16b, 16band exposed on the outer surface of the backsheet 3. The transversely intermediate portions 15a, 16a intersect each other in the vicinity of the longitudinal center line Y—Y and the transversely opposite end portions 15b, 15b; 16b, 16b are disposed between the backsheet 3 and the tissue paper 4 and secured to the absorbent sheet 4 by means of adhesive (not shown). The elastic fastening members 15, 16 are dimensioned so that the respective transversely intermediate portions 15a, 16a extend between the transversely opposite side edges 5a, 5a of the core 5, i.e., the intermediate portions 15a, 16a are dimensioned to be substantially equal to each other.

As shown by FIG. 8, the diaper 1 is rolled up, in the longitudinal direction, from the crotch region 31 toward the waist-hole 6 with the waist-hole facing outside. The stretched elastic fastening members 15, 16 are wound around the outer peripheral surface of the rolled up diaper 1 as the transversely intermediate portions 15a, 16a of the respective elastic members 15, 16 are caught by the hook member 11.

The transversely intermediate portions 15a, 16a of the respective elastic fastening members 15, 16 are branched by the hook member 11 in two sections 15a, 15a; 16a, 16a, respectively. Each pair of the branched sections 15a, 16a are placed one upon another so that the elastic members 15, 16 may further securely collapse the waist-hole 6 and restrain hole 6 from being opened.

The topsheet 2 may be formed using a liquid-pervious sheet such as a nonwoven fabric or porous plastic film, preferably using a liquid-pervious and hydrophilic sheet. The backsheet 3 may be formed using a hydrophobic nonwoven fabric, liquid-impervious plastic film or a laminated sheet consisting of a hydrophobic nonwoven fabric and plastic film, preferably using a breathable but liquid-impervious sheet.

The nonwoven fabric used for the purposes as described above may be selected from a group including a spun lace nonwoven fabric, needle punch nonwoven fabric, melt blown nonwoven fabric, thermal bond nonwoven fabric, spun bond nonwoven fabric and chemical bond nonwoven fabric. Component fiber of the nonwoven fabric may be selected from a group including polyolefine, polyester and polyamide fibers and a conjugated fiber of polyethylene/polypropyrene or polyester.

The core 5 may be provided in the form of a mixture of fluff pulp and highly absorptive polymer particles compressed to a desired thickness. The elastic members 10, 14, 15, 16 for fastening the used diaper 1 in its rolled up state may be formed using a thread- or band-like elastomer made of synthetic or natural rubber, or such an elastomer secured under tension to a nonwoven fabric strip. Operation of attaching the elastic members 10, 14, 15, 16 may be carried out using adhesive such as hot melt adhesive or pressure-sensitive adhesive and/or heat-sealing technique.

It is possible without departing from the scope and the spirit of this invention to bond the transversely opposite end portions 10b, 10b; 14b, 14b; 15b, 15b; 16b, 16b of the elastic members 10, 14, 15, 16 to the outer surface of the backsheet 3 instead of disposing the transversely opposite end portions between the backsheet 3 and the tissue paper 4.

The transversely intermediate portions 10a, 14a, 15a, 16a may have an elastic stretchability sufficient to make a complete round or more on the outer peripheral surface of the rolled up diaper 1. The elastic fastening members 10, 14, 15, 16 may be wound around the outer peripheral surface of the rolled up diaper 1 two or more times to reduce the bulkiness of the rolled up diaper 1.

What is claimed is:

1. A disposable pull-on diaper, comprising a diaper body, at least one elastically stretchable fastening member, and a hook member; wherein said diaper body has, in a longitudinal direction thereof, a front waist region, a rear waist region and a crotch region extending therebetween;

said diaper body comprises a liquid-pervious topsheet, a liquid-impervious backsheet and a liquid-absorbent core disposed between the topsheet and backsheet;

said front and rear waist regions are joined together along respective transversely opposite side edges thereof to define a waist-hole and a pair of leg-holes;

said at least one elastically stretchable fastening member is provided on one of a front half of said diaper body which front half extends from a transverse center line of said diaper bisecting said crotch region toward said front waist region, and a rear half of said diaper body which rear half extends from said transverse center line toward said rear waist region;

said at least one elastically stretchable fastening member extends transversely of said diaper body across a longitudinal center line bisecting a dimension between said transversely opposite side edges of said front and rear waist regions;

said at least one elastically stretchable fastening member comprises opposite end portions and an intermediate portion extending between said opposite end portions;

said opposite end portions are directly secured to said diaper body whereas said intermediate portion is not directly secured to and separable from said diaper body;

said intermediate portion of said fastening member is exposed on an outer surface of said backsheet; and said hook member is provided on said longitudinal center line in said one of said front and rear halves to catch said intermediate portion of said fastening member when said diaper body is rolled up, after use, with said intermediate portion of said fastening member extending around the rolled diaper body.

2. The diaper according to claim 1, wherein said at least one elastically stretchable fastening member includes at least a pair of elastically stretchable fastening members extending in parallel and spaced from each other in said longitudinal direction.

3. The diaper according to claim 2, wherein the intermediate portions of said pair of elastically stretchable fastening members have different dimensions.

4. The diaper according to claim 1, wherein said at least one elastically stretchable fastening member includes at least a pair of elastically stretchable fastening members, the intermediate portions of said pair of elastically stretchable fastening members intersect each other in a vicinity of said longitudinal center line.

5. The diaper according to claim 1, wherein said intermediate portion extends between transversely opposite side edges of said core.

6. The diaper according to claim 1, wherein said at least one fastening member is secured under no tension to said diaper body.

7. A disposable pull-on diaper, comprising a diaper body and securing means for securing said diaper body in a rolled-up state, after use; wherein said diaper body has, in a longitudinal direction thereof, a front waist region, a rear waist region and a crotch region extending therebetween, said front and rear waist regions being joined together along respective transversely opposite side edges thereof to define a waist-hole and a pair of leg-holes;

said securing means includes an elastically stretchable fastening member and a hook member;

said elastically stretchable fastening member is provided in an upper zone of one of said front and rear waist regions and extends transversely of said diaper body, opposite ends of said elastically stretchable fastening member are secured to said diaper body at locations adjacent the transversely opposite side edges of said front and rear waist regions; and said hook member is provided in a middle zone of said one of said front and rear waist regions between said elastically stretchable fastening member and said crotch region, so as to hook said elastically stretchable fastening member which extends around said rolled-up diaper body, after use.

8. The diaper according to claim 7, wherein said diaper body has an outer surface and an inner surface, said opposite ends of said elastically stretchable fastening member are laid between the outer and inner surfaces, said elastically stretchable fastening member further includes a middle portion extending between said opposite ends, said middle portion is exposed on the outer surface of said diaper body in said one of said front and rear waist regions.

* * * * *